US009867628B2

(12) United States Patent
Macke

(10) Patent No.: US 9,867,628 B2
(45) Date of Patent: Jan. 16, 2018

(54) DEVICE FOR EXTRACTION OF PROSTHETIC IMPLANTS

(71) Applicant: Zimmer, Inc., Warsaw, IN (US)

(72) Inventor: Jacob Macke, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 585 days.

(21) Appl. No.: 14/502,329

(22) Filed: Sep. 30, 2014

(65) Prior Publication Data

US 2015/0127010 A1 May 7, 2015

Related U.S. Application Data

(60) Provisional application No. 61/901,041, filed on Nov. 7, 2013.

(51) Int. Cl.
*A61B 17/17* (2006.01)
*A61F 2/46* (2006.01)
*A61F 2/36* (2006.01)

(52) U.S. Cl.
CPC ............ *A61B 17/1742* (2013.01); *A61F 2/36* (2013.01); *A61F 2002/4619* (2013.01)

(58) Field of Classification Search
CPC ....... A61B 17/15; A61B 17/151; A61B 17/17; A61B 17/1735; A61B 17/1739; A61B 17/1742; A61B 17/175; A61F 2/4607; A61F 2002/4619
USPC .............................................. 606/87, 89, 99
See application file for complete search history.

(56) References Cited

U.S. PATENT DOCUMENTS

| | | | | | |
|---|---|---|---|---|---|
| 4,562,598 A | * | 1/1986 | Kranz | ................ | A61B 17/8808 623/18.11 |
| 4,686,971 A | * | 8/1987 | Harris | ................... | A61F 2/4607 606/99 |
| 4,993,410 A | * | 2/1991 | Kimsey | ................. | A61F 2/4607 606/100 |
| 5,257,995 A | * | 11/1993 | Umber | ............... | A61B 17/8872 606/86 R |
| 5,569,255 A | * | 10/1996 | Burke | ................ | A61B 17/1659 606/79 |
| 5,674,225 A | * | 10/1997 | Muller | ............... | A61B 17/1659 606/100 |
| 5,743,910 A | * | 4/1998 | Bays | ..................... | A61F 2/4607 606/99 |
| 5,951,606 A | * | 9/1999 | Burke | ................ | A61B 17/1604 606/95 |
| 6,110,179 A | * | 8/2000 | Flivik | ............... | A61B 17/8808 606/94 |
| 6,113,605 A | * | 9/2000 | Storer | .................. | A61F 2/4607 606/86 R |

(Continued)

FOREIGN PATENT DOCUMENTS

WO    WO-2012006508 A2    1/2012

*Primary Examiner* — Eric S Gibson
(74) *Attorney, Agent, or Firm* — Schwegman Lundberg & Woessner, P.A.

(57) ABSTRACT

A surgical cutting guide includes a guide body removably attachable to a proximal end of an implanted prosthesis. The guide body has at least one locator configured to azimuthally orient the guide body with respect to the prosthesis. The guide body has at least one slot extending from a proximal side of the guide body to a distal side of the guide body. A method of removing an implanted prosthesis can attach a surgical cutting guide to an implanted prosthesis with a specified azimuthal orientation, can direct an osteotome through a slot in the surgical cutting guide to a specified location at or near an interface between the prosthesis and the bone, can dislodge the prosthesis from the bone using the osteotome, can retract the osteotome through the slot, and can remove the dislodged prosthesis from the bone.

15 Claims, 6 Drawing Sheets

(56) References Cited

U.S. PATENT DOCUMENTS

| | | | |
|---|---|---|---|
| 6,187,012 B1* | 2/2001 | Masini | A61B 17/15 606/99 |
| 7,935,118 B2* | 5/2011 | Vendrely | A61B 17/17 606/87 |
| 8,372,077 B2 | 2/2013 | Taylor | |
| 8,414,585 B2 | 4/2013 | Meneghini et al. | |
| 8,449,550 B2* | 5/2013 | Talamini | A61B 17/15 606/79 |
| 2003/0236525 A1* | 12/2003 | Vendrely | A61B 17/17 606/87 |
| 2004/0015238 A1* | 1/2004 | Buehler | A61B 17/8808 623/22.12 |
| 2004/0162619 A1* | 8/2004 | Blaylock | A61B 17/1764 623/20.16 |
| 2008/0172061 A1* | 7/2008 | Ragbir | A61F 2/4603 606/99 |
| 2009/0018546 A1* | 1/2009 | Daley | A61B 17/175 606/92 |
| 2011/0009976 A1* | 1/2011 | Cruchet | A61B 17/1668 623/22.46 |
| 2011/0208201 A1* | 8/2011 | Daley | A61B 17/175 606/89 |
| 2012/0116406 A1* | 5/2012 | Talamini | A61B 17/15 606/88 |
| 2015/0057666 A1* | 2/2015 | Kelley | A61B 17/1735 606/87 |
| 2015/0127010 A1* | 5/2015 | Macke | A61B 17/1742 606/88 |

* cited by examiner

DEVICE FOR EXTRACTION OF PROSTHETIC IMPLANTS

CLAIM OF PRIORITY

This application claims the benefit of U.S. Provisional Patent Application Ser. No. 61/901,041, filed on Nov. 7, 2013, the benefit of priority of which is claimed hereby, and which is incorporated by reference herein in its entirety.

TECHNICAL FIELD

The present patent application relates to the field of orthopedics, and more specifically, to the removal of surgically implanted orthopedic prostheses.

BACKGROUND

A human hip joint connects a femur (sometimes referred to as a thigh bone) to an acetabulum (sometimes referred to as a hip socket) of the pelvis. Hip joints support the weight of a human body, and are important for retaining balance.

Some types of injury, disease, or degeneration can produce pain and/or restricted motion in a hip joint. When severely damaged, in one treatment option, the natural hip joint can be surgically replaced with a prosthetic hip joint in a procedure known as total joint arthroplasty (TJA). The prosthetic joint generally has two parts, an acetabular prosthesis and a femoral prosthesis, which are implanted into a patient's pelvis and femur, respectively.

During implantation, the acetabular and femoral prosthesis components are secured to their adjacent bone. For example, surgeons often use bone cement to position a femoral prosthesis component in a patient's femoral intramedullary canal. Alternatively or additionally, the femoral prosthesis component may include a porous outer coating that allows for bone ingrowth into the prosthesis components, so that the components can join with the bone over time in a cementless interface.

Many patients successfully treated with TJA return to active lifestyles. However, in some patients, the prosthetic joint can fail, requiring further medical intervention, often referred to as a revision procedure, to remove and replace the prosthesis components. Removal of firmly implanted prosthetic joint components can be difficult.

OVERVIEW

A surgical cutting guide includes a guide body removably attachable to a proximal end of an implanted prosthesis. The guide body has at least one locator configured to azimuthally orient the guide body with respect to the prosthesis. The guide body has at least one slot extending from a proximal side of the guide body to a distal side of the guide body. A method of removing an implanted prosthesis can attach a surgical cutting guide to an implanted prosthesis with a specified azimuthal orientation, can direct an osteotome through a slot in the surgical cutting guide to a specified location at or near an interface between the prosthesis and the bone, can dislodge the prosthesis from the bone using the osteotome, can retract the osteotome through the slot, and can remove the dislodged prosthesis from the bone.

The locator can include one or more recesses configured to removably engage one or more protuberances on the prosthesis. The locator can include one or more protuberances configured to removably engage one or more recesses on the prosthesis. The locator can include a cavity extending into the distal side of the guide body. The cavity can be sized and shaped to intimately contact the proximal end of the prosthesis, and/or can include one or more regions that are shaped to intimately contact the proximal end of the prosthesis.

Although the surgical cutting guides of the present application are described and shown in use with a femoral prosthesis, it is recognized that the surgical cutting guides can be used with other types of prostheses, such as, for example shoulder stems.

This overview is intended to provide an overview of subject matter of the present patent application. It is not intended to provide an exclusive or exhaustive explanation of the invention. The Detailed Description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
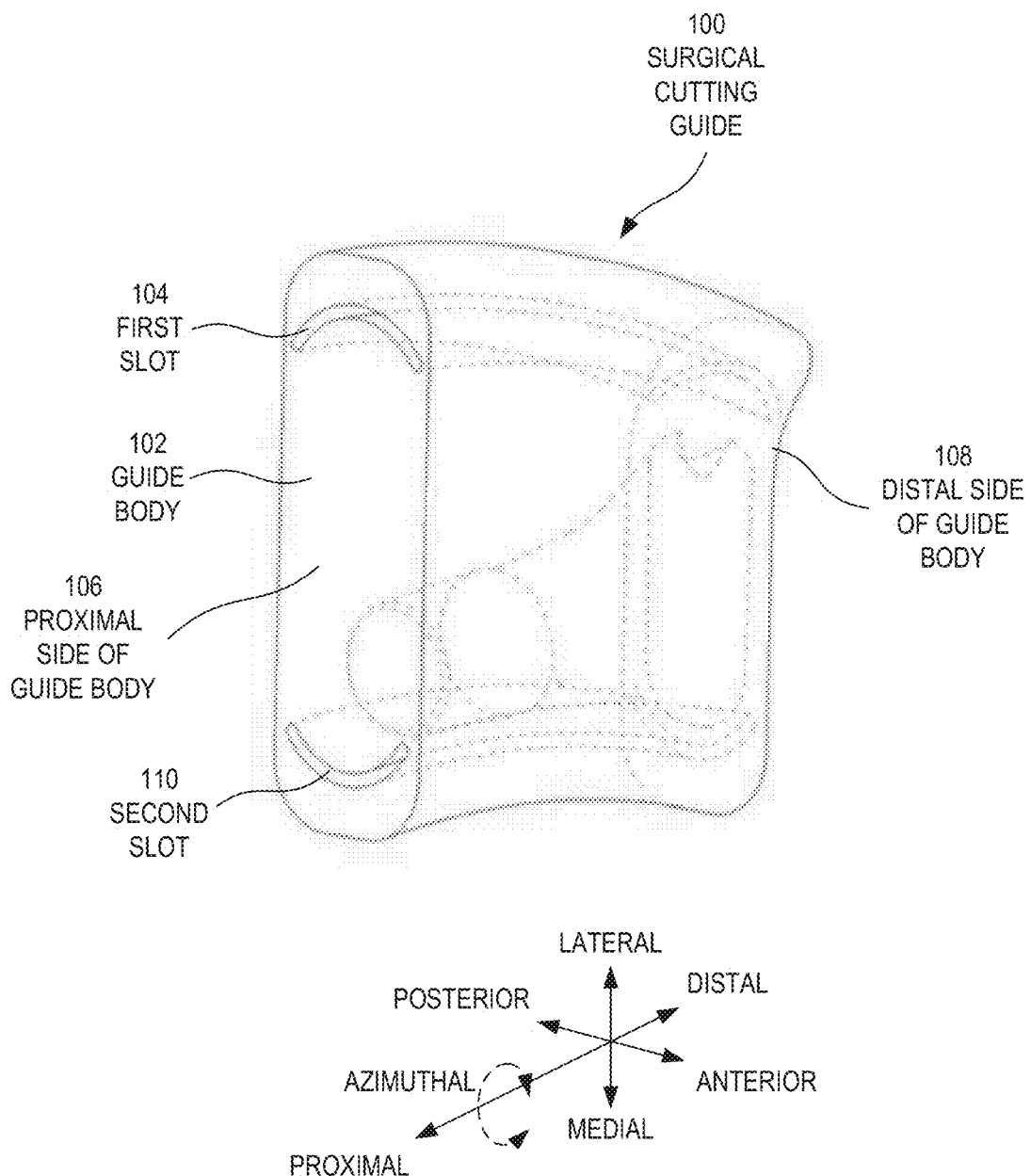
FIG. 1 is an isometric view of an example of a surgical cutting guide.

FIG. 1 shows an isometric view of an example of a surgical cutting guide 100 for directing an osteotome or other cutting instrument to an interface between an implanted prosthesis and a patient's bone. The prosthesis can be implanted in the patient's femur, or in any suitable bone. FIG. 1 includes anatomical directions that can describe a location or position of the prosthesis when implanted, including proximal/distal, medial/lateral, and anterior/posterior. FIG. 1 also shows an azimuth orientation relative to the proximal/distal, medial/lateral, and anterior/posterior directions. As used herein, the azimuthal orientation is a rotational orientation with respect to a defined axis parallel to a proximal stem (see proximal stem 321 in FIG. 3) on the implanted prosthesis. The azimuthal orientation is used herein to describe a position that can be lateral, medial, posterior or anterior to the defined axis.

The surgical cutting guide 100 can include a guide body 102 that is removably attachable to a proximal end of an implanted prosthesis. The guide body 102 can be formed as a unitary element, or can be formed as a plurality of elements that are attached to one another. In some examples, the guide body 102 can have a generally rectangular exterior shape, where opposing sides are parallel to each other and are orthogonal to adjacent sides. In some examples, the rectangular exterior shape can be convenient for gripping or for storage. In some examples, some or all of the edges of the guide body 102 can be rounded. In other examples, the guide body 102 can have any suitable exterior shape. The guide body 102 can be formed from metal, plastic, or any suitable material for use in a body of a human or an animal. In some examples, the guide body 102 can be formed from a biocompatible material.

The guide body 102 can include a first slot 104 extending from a proximal side 106 of the guide body 102 to a distal side 108 of the guide body 102 and configured to receive an osteotome. The first slot 104 is positioned azimuthally, on a lateral side of the guide body 102, to guide the osteotome toward a lateral side of the prosthesis. The first slot 104 extends generally longitudinally from the proximal side 106 to the distal side 108, so that the first slot 104 resides in a single plane that includes the lateral/medial directions and the proximal/distal directions. When the surgical cutting guide 100 is attached to a prosthesis, a distal end of the first slot 104 is disposed at or near an interface between the prosthesis and the bone. The first slot 104 can have a slight curvature within the plane, so that when viewed from the lateral direction toward the medial direction, the curvature along the proximal/distal direction is convex, while the curvature along the posterior/anterior direction is convex. Such a curvature can be useful for imparting a shape to an osteotome that is inserted through the first slot 104, to guide the osteotome to a location near, but distal to, a distal end of the guide body 104, at an interface between a lateral side of the implanted prosthesis and the bone. In some examples, the first slot 104 has a constant curvature along its longitudinal extent. In other examples, the first slot 104 has a curvature that varies along its longitudinal extent. In other examples, the first slot 104 is straight along its longitudinal extent. In still other examples, the first slot 104 includes at least one convex portion, at least one straight portion, or one concave portion along its longitudinal extent. The first slot 104 can have an elongated cross-section, being wider in an anterior/posterior direction than in the lateral/medial direction. In some examples, the relatively narrow lateral/medial extent of the first slot 104 can desirably restrict any lateral/medial movement of the osteotome therethrough. Note that FIG. 1 is drawn for a left hip prosthesis; a right hip prosthesis would look similar, but with the anterior and posterior directions reversed. In some examples, the first slot 104 has a uniform cross-section along its longitudinal extent. In other examples, the first slot 104 has a cross-section that varies along its longitudinal extent. In other examples, the first slot 104 has a cross-section profile that is generally curved about an axis generally parallel to a proximal stem. In some examples, the first slot 104 has a length configured to limit motion of the osteotome to a specified distal depth within the interface between the lateral side of the implanted prosthesis and the bone.

The guide body 102 also includes a second slot 110 extending from the proximal side 106 of the guide body 102 to the distal side 108 of the guide body 102. The second slot 110 can be similar in structure and function to the first slot 104, but positioned on the medial side of the guide body, to guide an osteotome toward a medial side of the prosthesis, at an interface between the lateral side of the prosthesis and the bone. In some examples, the second slot 110 is curved within a single plane, so that when viewed from the medial direction towards the lateral direction, the curvature along the proximal/distal direction is concave, while the curvature along the posterior/anterior direction is convex. In some examples, the second slot 110 slot has a length configured to limit motion of the osteotome to a specified distal depth within the interface between the medial side of the implanted prosthesis and the bone.

In the example of FIG. 1, the guide body 102 includes two slots 104, 110 extending therethrough; in other examples the guide body 102 can include one, at least one, three, four, five, six, or more than six slots extending therethrough. Each slot can have a corresponding azimuthal location, so that collectively, the slots can provide access to a full circumference around the implanted prosthesis.

Figure 2:
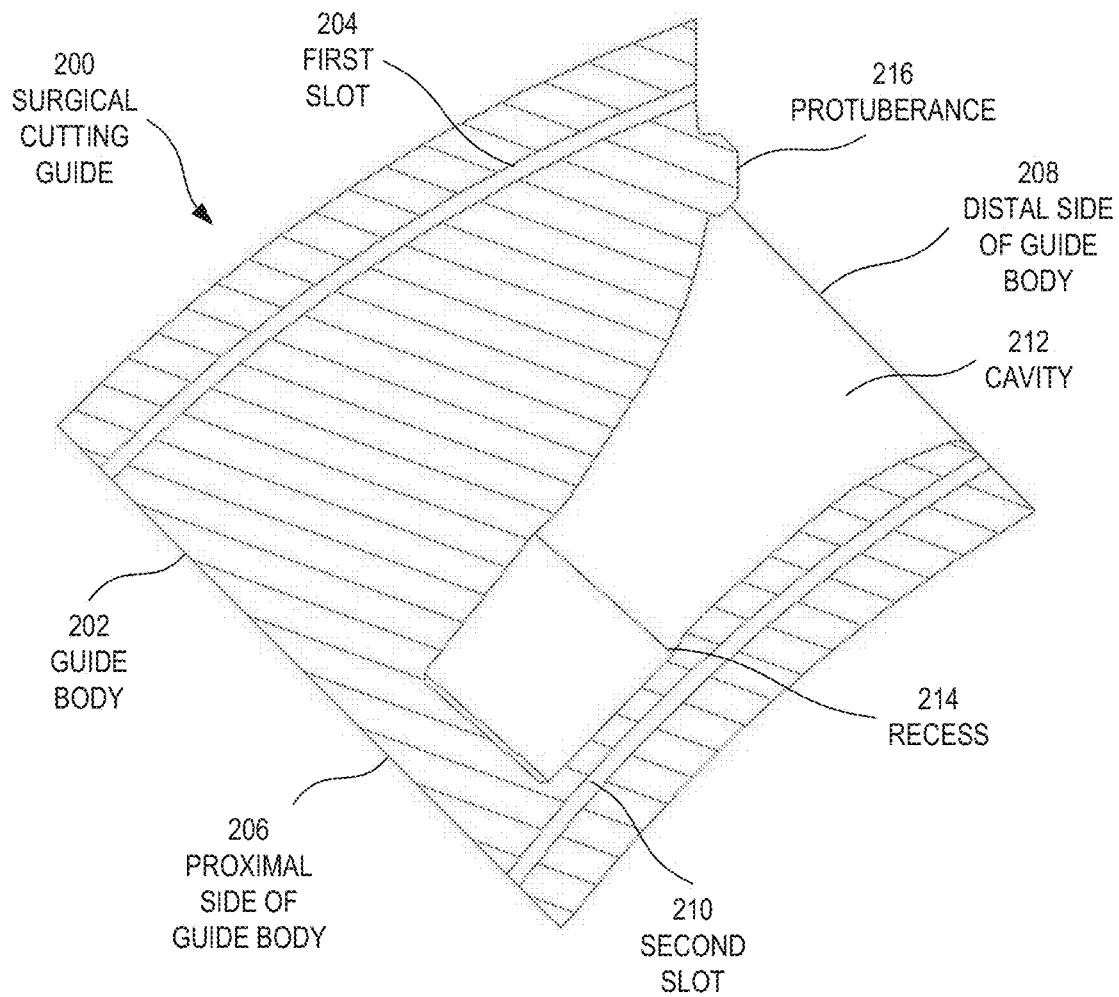
FIG. 2 is a cross sectional view of an example of a surgical cutting guide.
Figure 2:
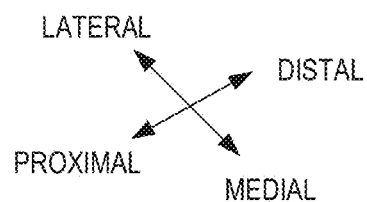

FIG. 2 shows an example of a surgical cutting guide 200 in a cross-section taken in a plane that includes the lateral/medial directions and the proximal/distal directions. Elements numbered as 2xx in FIG. 2 are similar in structure and function to corresponding elements numbered as 1xx in FIG. 1.

When the surgical cutting guide 200 is attached to the prosthesis, it can be beneficial for the surgical cutting guide 200 have a specified azimuthal orientation with respect to the prosthesis. For example, when attached, a medial side of the surgical cutting guide 200 is aligned to a medial side of the prosthesis, and a lateral side of the surgical cutting guide 200 is aligned to a lateral side of the prosthesis. A guide body 202 includes at least one locator that can azimuthally align the guide body 202 to the prosthesis during attachment, so that the attachment occurs at only one specified azimuthal orientation, or at one of a plurality of specified azimuthal orientations.

An example of a locator is a cavity 212 that extends from a distal side 208 of the guide body 202 and toward (or through) the proximal side 206 of the guide body 202. The cavity 212 can be sized and shaped to intimately contact a proximal end of the prosthesis. In some examples, the cavity 212 forms a press fit with the proximal end of the prosthesis. In other examples, the cavity 212 includes geometry that azimuthally aligns with the proximal end of the prosthesis, but without forming a press fit. In this example, the cavity 212 is shaped so that the surgical cutting guide 200 fits onto the prosthesis in only one azimuthal orientation. In other examples, the cavity 212 can be shaped so that the surgical cutting guide 200 fits onto the prosthesis in only two azimuthal orientations, three azimuthal orientations, or one of a finite number of azimuthal orientations. In some examples, the cavity 212 includes three or more points of contact with the prosthesis. Another example of a locator is one or more matched pairs of recesses 214 and protuberances 216 located on the guide body 202 and the prosthesis. For example, a peg extending from the guide body 202 can fit into a corresponding slot in the prosthesis only when the guide body 202 is azimuthally aligned to the prosthesis. As another example, a round protuberance on the prosthesis can fit into a corresponding round indentation on the guide body 202. In general, the locator includes one or more protuberances configured to removably engage one or more recesses, to azimuthally orient the guide body 202 with respect to the prosthesis. The protuberances can be on the guide body 202 or the prosthesis, and the corresponding recesses can also be on the guide body 202 or the prosthesis. In some examples, at least one of the protuberances or recesses is disposed on the inside of the cavity 212.

Figure 3:
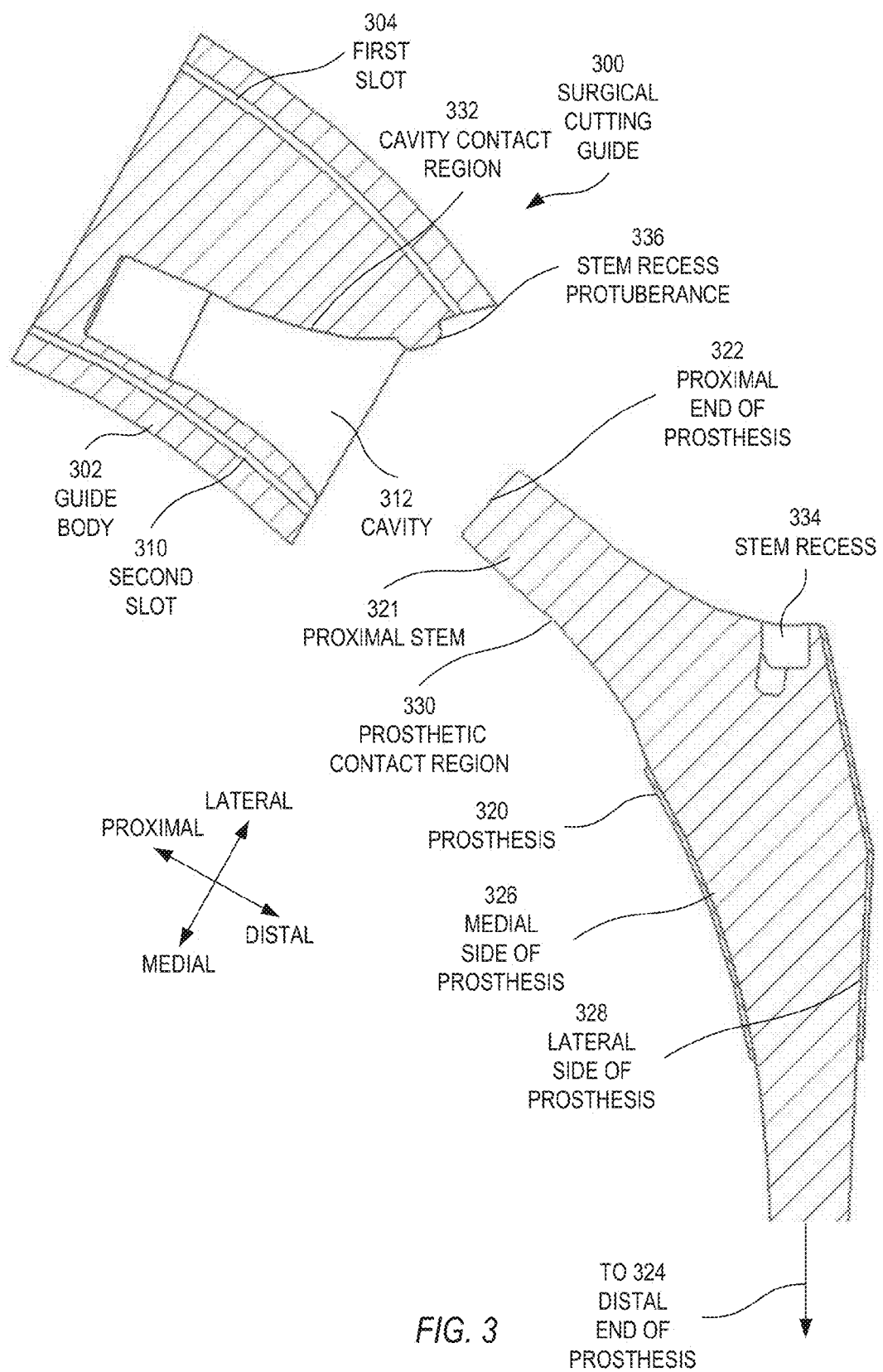
FIG. 3 is an exploded cross sectional view of an example of a surgical cutting guide and an example of an implanted femoral prosthesis.

FIG. 3 shows an example of a surgical cutting guide 300 in a cross-section taken in a plane that includes the lateral/medial directions and the proximal/distal directions, and a corresponding cross-section of a prosthesis 320, prior to removably attaching the surgical cutting guide 300 to the prosthesis 320. The prosthesis 320 is not part of the surgical cutting guide 300. Elements numbered as 3xx in FIG. 3 are similar in structure and function to corresponding elements numbered as 2xx in FIG. 2.

The prosthesis 320 includes a proximal end 322, a distal end 324, a medial side 326, and a lateral side 328. The proximal end 322 of the prosthesis 320 includes prosthesis contact regions 330 that are shaped to contact corresponding guide contact regions 332 in the cavity 312 of the guide body 302. In the example of FIG. 3, the contact regions 330, 332 are shaped to fully contact each other; in other examples, the contact regions can include specific points of contact. The shaping of the contact regions 330, 332, taken together, form a locator, which azimuthally orients the guide body 302 with respect to the prosthesis 320.

The proximal end 322 of the prosthesis 320 can include a stem recess 334. In some examples, the stem recess 334 is located directly proximal to the distal end 324 of the prosthesis, and extends distally toward the distal end 324 of the prosthesis 320. In some examples, the guide body 302 is shaped to include a stem recess protuberance 336. When the guide body 302 is attached to the prosthesis, the stem recess protuberance 336 engages the stem recess 334. The stem recess protuberance 336 and the stem recess 334, taken together, form a locator, which azimuthally orients the guide body 302 with respect to the prosthesis 320.

Figure 4:
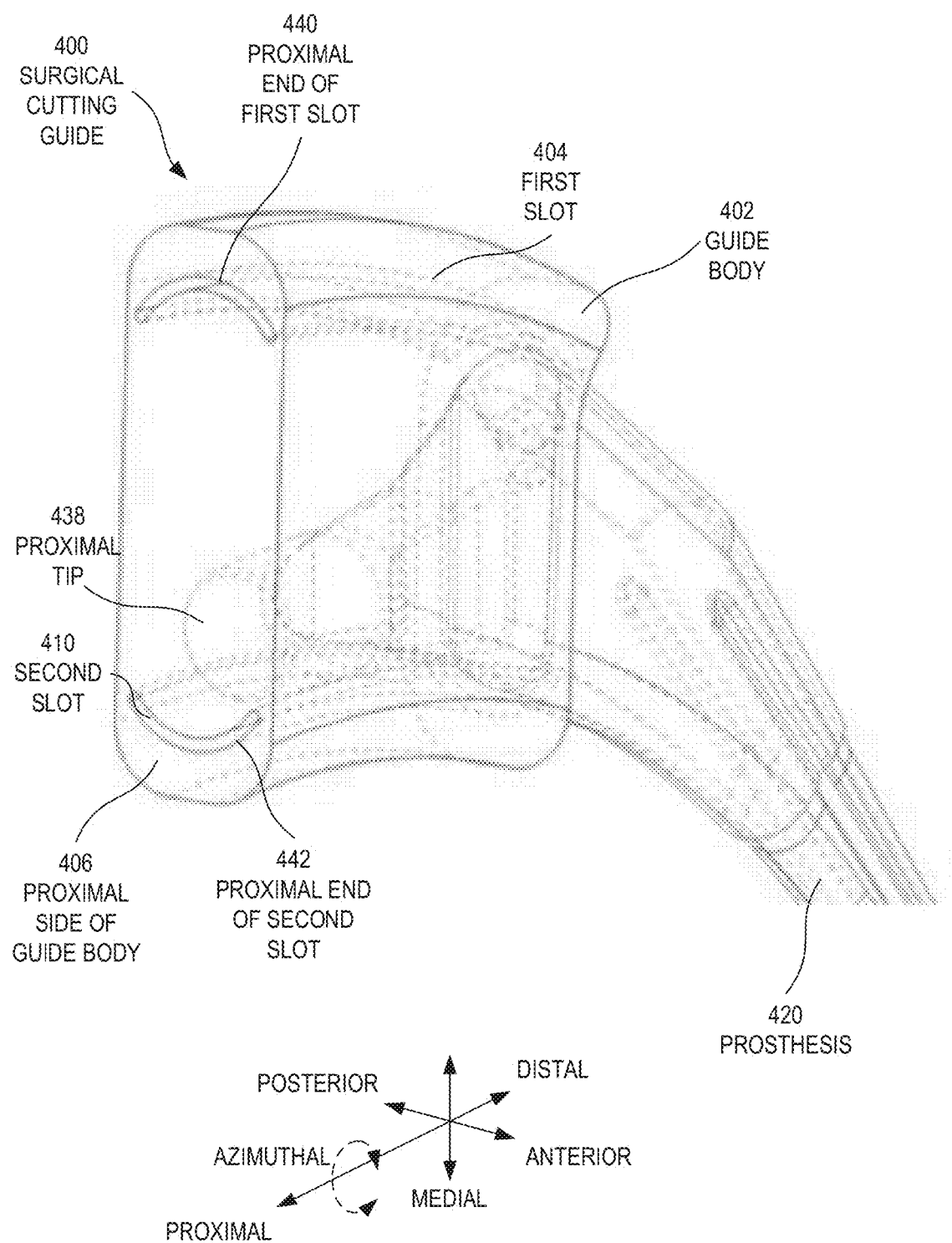
FIG. 4 is an isometric view of an example of a surgical cutting guide removably engaged with an example of an implanted femoral prosthesis.

FIG. 4 shows an isometric view of an example of a surgical cutting guide 400 removably attached to, and azimuthally oriented with respect to, a prosthesis 420. In the example of FIG. 4, a proximal tip 438 of the proximal end of the prosthesis 420 can be located distal to the proximal side 406 of the guide body 402 when the surgical cutting guide 400 is attached to the prosthesis 420. In other configurations, the proximal tip 438 can be flush with the proximal side 406 of the guide body 402, or can be located to extend proximally beyond a proximal side 406 of the guide body 402 when the surgical cutting guide 400 is attached to the prosthesis 420. Proximal ends 440, 442 of the first and second slots 402, 410 are visible in FIG. 4. Elements numbered as 4xx in FIG. 4 are similar in structure and function to corresponding elements numbered as 3xx in FIG. 3.

Figure 5:
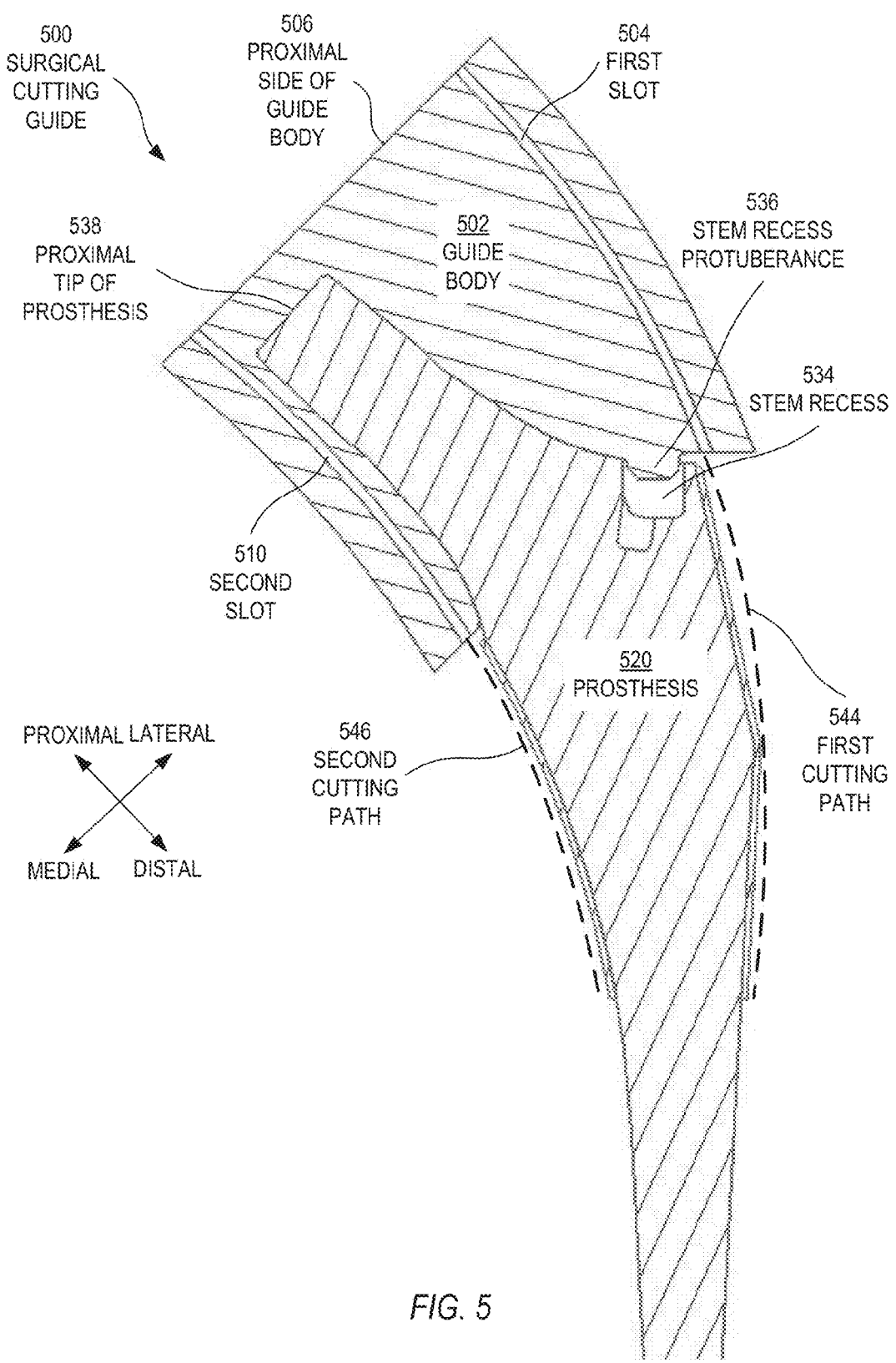
FIG. 5 is a cross sectional view of the surgical cutting guide removably engaged with the femoral prosthesis of FIG. 4.

FIG. 5 shows a cross-section, taken in a plane that includes the lateral/medial directions and the proximal/distal directions, of an example of a surgical cutting guide 500, removably attached to an implanted prosthesis 520. A first slot 504 can guide an osteotome along a first cutting path 544, at an interface between a lateral side of the prosthesis 520 and the adjacent portion of bone. In some examples, the first slot 504 has a curvature that can direct the first cutting path to closely track the interface between the prosthesis 520 and the bone. This close tracking can reduce or minimize bone loss during extraction of the prosthesis 520, which is desirable. Similarly, a second slot 510 can guide an osteotome along a second cutting path 546, at an interface between a medial side of the prosthesis 520 and the adjacent portion of bone. In the example of FIG. 5, the proximal tip 538 of the prosthesis 520 is contained within the guide body 502, and is distal to the proximal side 506 of the guide body 502. Elements numbered as 5xx in FIG. 5 are similar in structure and function to corresponding elements numbered as 4xx in FIG. 4.

In some examples, femoral stems (or other suitable stems, such as shoulder stems) can be sized as one of a plurality of discrete sizes. Prior to, or during, implantation surgery, a practitioner selects one of the discrete sizes to best match an anatomy of a patient. In some examples, the medial sides of the stems are all sized and shaped the same, for all discrete sizes in the plurality, although the medial sides may also be sized and shaped differently for the discrete sizes. In some examples, each discrete size has a corresponding surgical cutting guide. In some examples, the surgical cutting guide is modular, so that a single surgical cutting guide can accommodate the discrete sizes in the plurality. In some examples, a surgical cutting guide can include multiple slots at a particular azimuthal location, where each size in the plurality has a corresponding slot on the surgical cutting guide.

Figure 6:
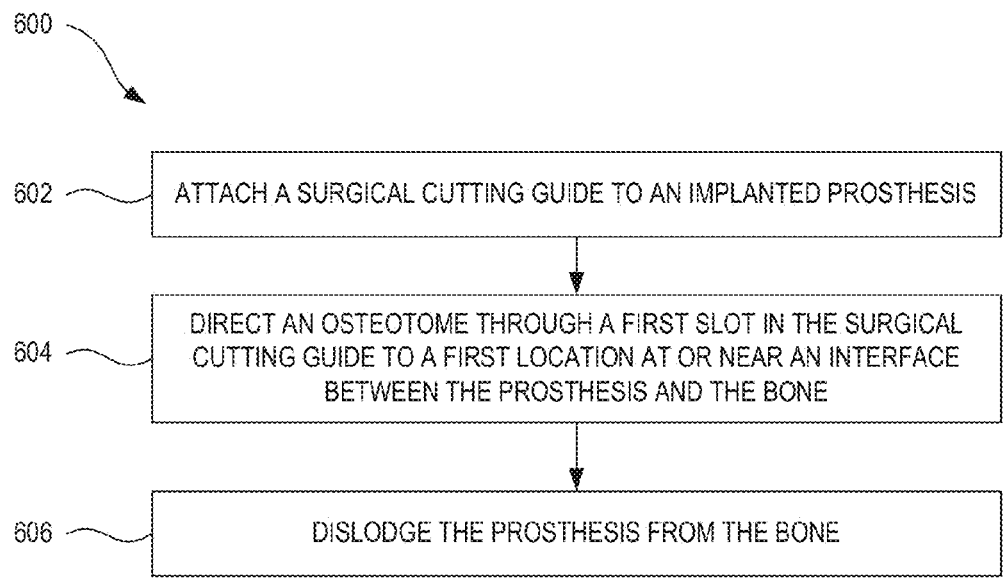
FIG. 6 is a flow chart of an example of a method of operation of a surgical cutting guide.

FIG. 6 is a flow chart of an example of a method 600 for using a surgical cutting guide to remove an implanted prosthesis implanted in a bone. Step 602 attaches the surgical cutting guide to an implanted prosthesis. The surgical cutting guide attaches to the prosthesis at one or more specified azimuthal orientations with respect to the implanted prosthesis, using, for example, one or more locators, as described above. Step 604 directs an osteotome through a first slot in the surgical cutting guide to a first specified location at or near an interface between the implanted prosthesis and the bone. In some examples, step 604 can be repeated as needed, optionally through different slots in the surgical cutting guide that have different azimuthal orientations. The different azimuthal orientations can provide access at various locations around a circumference of the implanted prosthesis. Step 606 dislodges the implanted prosthesis using the osteotome. Once the prosthesis is dislodged, the osteotome can be retracted through the first slot, and the dislodged prosthesis can be removed from the bone. In some examples, the surgical cutting guide is first removed from the prosthesis, then the prosthesis is removed from the bone. In other examples, the surgical cutting guide remains attached to the prosthesis, and the surgical cutting guide and the prostheses, together, are removed from the bone.

The above Detailed Description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, assembly, device, kit, article, or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A surgical cutting guide for removing a prosthesis implanted in a bone, the prosthesis having a proximal end, a distal end, a medial side and a lateral side, the surgical cutting guide comprising:
   a guide body removably attachable to the proximal end of the prosthesis, the guide body having at least one locator configured to azimuthally orient the guide body with respect to the prosthesis, the at least one locator including one or more recesses to removably engage one or more protuberances on the prosthesis to azimuthally orient the guide body with respect to the prosthesis, and
   the guide body having at least one slot extending from a proximal side of the guide body to a distal side of the guide body, the at least one slot being curved with a curvature configured to direct an osteotome along a curved cutting path in a proximal to distal direction to an interface between the bone and one of the medial side of the implanted prosthesis or the lateral side of the implanted prosthesis.

2. The surgical cutting guide of claim 1, wherein the at least one locator further includes one or more protuberances to removably engage one or more recesses on the prosthesis to azimuthally orient the guide body with respect to the prosthesis.

3. The surgical cutting guide of claim 1, wherein the at least one locator comprises a cavity extending into the distal side of the guide body, the cavity being sized and shaped to intimately contact the proximal end of the prosthesis to azimuthally orient the guide body with respect to the prosthesis.

4. The surgical cutting guide of claim 3, wherein the guide body includes one or more protuberances to removably engage one or more recesses on the prosthesis to azimuthally orient the guide body with respect to the prosthesis.

5. The surgical cutting guide of claim 3, wherein the cavity includes one or more recesses to removably engage one or more protuberances on the prosthesis to azimuthally orient the guide body with respect to the prosthesis.

6. The surgical cutting guide of claim 3, wherein the cavity includes one or more protuberances to removably engage one or more recesses on the prosthesis to azimuthally orient the guide body with respect to the prosthesis, the cavity including one or more recesses to removably engage one or more protuberances on the prosthesis to azimuthally orient the guide body with respect to the prosthesis.

7. The surgical cutting guide of claim 1, wherein the at least one slot has a length configured to limit motion of the osteotome to a specified distal depth within the interface between the bone and one of the medial side of the implanted prosthesis or the lateral side of the implanted prosthesis.

8. The surgical cutting guide of claim 1, wherein the at least one slot comprises a first slot and a second slot, each extending from the proximal side of the body to the distal side of the body, the first and second slots having different azimuth orientations.

9. The surgical cutting guide of claim 8,
   wherein the first slot is curved, the curvature being configured to direct an osteotome to an interface between the lateral side of the prosthesis and the bone; and
   wherein the second slot is curved, the curvature being configured to direct an osteotome to an interface between the medial side of the prosthesis and the bone.

10. The surgical cutting guide of claim 8,
    wherein the first slot has a length configured to limit motion of the osteotome to a specified depth within the interface between the lateral side of the prosthesis and the bone; and
    wherein the second slot has a length configured to limit motion of the osteotome to a specified depth within the interface between the medial side of the implanted prosthesis and the bone.

11. A surgical cutting guide for removing a prosthesis implanted in a bone, the prosthesis having a proximal end, a distal end, a medial side and a lateral side, the guide comprising:
    a guide body removably attachable to the proximal end of the prosthesis, the guide body having at least one locator to azimuthally orient the guide body with respect to the prosthesis, the at least one locator including one or more recesses to removably engage one or more protuberances on the prosthesis to azimuthally orient the guide body with respect to the prosthesis,
    the guide body having a lateral slot extending from a proximal side of the guide body to a distal side of the guide body, the lateral slot being curved with a curvature configured to direct an osteotome along a curved cutting path in a proximal to distal direction to an interface between the lateral side of the prosthesis and the bone; and
    the guide body having a medial slot extending from the proximal side of the guide body to the distal side of the guide body, the medial slot being curved with a curvature configured to direct an osteotome along a curved cutting path in the proximal to distal direction to an interface between the medial side of the prosthesis and the bone.

12. A method for using a surgical cutting guide to remove an implanted prosthesis implanted in a bone, the method comprising:
    attaching the surgical cutting guide to the implanted prosthesis, the surgical cutting guide including one or more recesses to removably engage one or more protuberances on the prosthesis to azimuthally align the surgical cutting guide with respect to the implant prosthesis;

directing an osteotome through a first slot extending from a proximal side of the surgical cutting guide to a distal side of the surgical cutting guide to a first specified location at or near an interface between the implanted prosthesis and the bone, the first slot being curved with a curvature to direct the osteotome along a curved cutting path in a proximal to distal direction to the first specified location; and dislodging the implanted prosthesis using the osteotome.

13. The method of claim 12, further comprising:

retracting the osteotome through the first slot.

14. The method of claim 13, further comprising:

removing the dislodged prosthesis from the bone.

15. The method of claim 13 further comprising:

directing the osteotome through a second slot in the surgical cutting guide to a second specified location at or near an interface between the implanted prosthesis and the bone, the first and second slots having different azimuthal orientations.

\* \* \* \* \*